United States Patent [19]

Cook

[11] Patent Number: 5,749,896

[45] Date of Patent: May 12, 1998

[54] STAPLE OVERLAP

[76] Inventor: Melvin S. Cook, 8 Saddle Ridge Rd., Hohokus, N.J. 07423

[21] Appl. No.: 786,195

[22] Filed: Jan. 21, 1997

Related U.S. Application Data

[63] Continuation of Ser. No. 502,988, Jul. 18, 1995, abandoned.

[51] Int. Cl.[6] ........................................... A61B 17/00
[52] U.S. Cl. ........................................... 606/219; 606/151
[58] Field of Search .................................. 606/219, 220, 606/139, 151, 157, 158, 75; 227/175.1–181.1, 19, 902

[56] References Cited

U.S. PATENT DOCUMENTS

| | | | |
|---|---|---|---|
| 4,526,174 | 7/1985 | Froelich | 606/219 |
| 4,607,638 | 8/1986 | Crainich | 606/219 |
| 4,702,247 | 10/1987 | Blake, III et al. | 606/157 |
| 4,874,122 | 10/1989 | Froelich et al. | 606/219 |
| 5,158,567 | 10/1992 | Green | 606/219 |
| 5,258,009 | 11/1993 | Conners | 606/219 |
| 5,342,395 | 8/1994 | Jarrett et al. | 606/219 |
| 5,366,479 | 11/1994 | McGarry et al. | 606/151 |
| 5,439,479 | 8/1995 | Shichman et al. | 606/220 |

FOREIGN PATENT DOCUMENTS

| | | | |
|---|---|---|---|
| 505036 | 9/1992 | European Pat. Off. | 606/219 |
| 0541950 | 5/1993 | European Pat. Off. | 606/219 |
| WO8200582 | 3/1982 | WIPO | 606/219 |

*Primary Examiner*—Jeffrey A. Schmidt
*Attorney, Agent, or Firm*—Kaplan & Gilman

[57] ABSTRACT

An improved stapling arrangement comprises a unique anvil which forces the ends of the staple legs to overlap when the staple is fully deformed.

2 Claims, 3 Drawing Sheets

STAPLE OVERLAP

This application is a continuation of Ser. No. 08/502,988 filed Jul. 18, 1995, now abandoned.

TECHNICAL FIELD

This invention relates to internal surgical stapling of soft tissues and, more particularly, to an improved stapling arrangement, staple and anvil which produce a deformed staple with leg overlap.

BACKGROUND OF THE INVENTION

Stapling of soft tissues during internal surgery are widely used techniques. Such stapling techniques typically use thin wire metal staples that, before installation, are substantially U-shaped, as shown in FIG. 1, and grooved anvils, as shown in FIGS. 3 and 4. The staple 11 shown in FIG. 1 includes a crown (back span) 4 and legs 7 with tips (ends) 9.

A plurality of staples typically are installed, either simultaneously or sequentially, by such surgical staplers. During staple installation, a staple pusher pushes on the crown 4 of the staple 11 and forces the tips 9 of the legs 7 through the tissue being stapled and then against an anvil. The staples may then be deformed to a B-shape, as shown in FIG. 2, as a result of interaction with the anvil.

The grooves 15 of anvil 17, shown in top view in FIG. 3 and in side crossectional view A–A' in FIG. 4, are shaped so as to achieve this desired deformation as the staple 11 is pushed against the anvil. The grooves 15 include narrow regions 19 of width 89 within which the legs 7 fit snugly during deformation of the staple 11. The width 89 of the narrow regions 19 is small in magnitude in order to so confine the legs 7 that the tips 9 butt up against each other and do not pass around each other. This is important in forcing deformation to the B-shaped configuration.

An improved thin wire metal staple for use in internal stapling is disclosed in U.S. Pat. No. 5,342,396 to Cook, the inventor of the present invention and in U.S. patent application Ser. No. 08/228,058 filed Apr. 15, 1994 by Cook now U.S. Pat. No. 5,445,698. Both of the aforementioned documents are incorporated herein by reference. The staples disclosed in both of these documents deform to somewhat of a rectangular shape when interacting with an anvil. One major advantage of such improved staples is that the tissue enclosed by the staple is substantially uniformly compressed, as discussed in the above-mentioned documents. Uniform compression is desirable in controlling blood flow so as to prevent tissue necrosis and/or bleeding and thereby assure optimum healing conditions.

It is an object of the present invention to provide a stapling arrangement including a specialized anvil and staple for use in internal surgery that helps obtain uniform tissue compression.

It is a further object of the present invention to provide an anvil for use in internal surgical stapling that allows the tips of the staple legs to pass around each other during staple deformation, i.e., that allows overlap of the staple legs ends.

It is a further object of the present invention to provide a surgical staple with deformation zones in its legs having sufficient lengths of legs extending beyond such deformation zones so that when the staples are deformed during installation the ends of the legs overlap.

It is an additional object of the present invention to provide a surgical staple with deformation zones in its legs so formed with respect to each other that they tend to bend the legs into different planes when interacting with an anvil.

SUMMARY OF THE INVENTION

The above and other objects of the invention are achieved in accordance with the present invention by use of a stapling arrangement which causes the staples to so deform that the ends of the legs of the deformed staple overlap each other. In a preferred embodiment, a staple of a type disclosed in U.S. Pat. No. 5,342,396 (a "Cook staple") includes leg lengths between the deformation zones and the leg tips (ends) which are sufficiently long that the tip of each deformed leg overlaps the tip of the other deformed leg.

DESCRIPTIONS OF THE PREFERRED EMBODIMENTS

Figure 7:
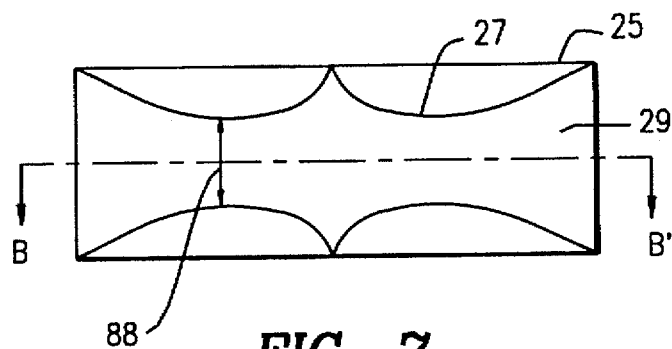
FIG. 7 shows an anvil for use with one embodiment of the present invention.
Figure 8:
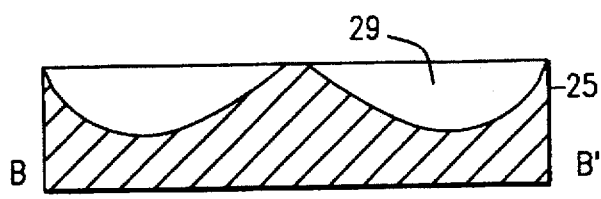
FIG. 8 shows a side cross section view B–B' of the anvil of FIG. 7.

FIG. 7 shows a top view of an anvil 25 used in a first exemplary embodiment of the present invention. The anvil 25 incorporates a groove 29 to effectuate staple deformation. A side crossectional view B–B' of the anvil 25 and groove 29 of FIG. 7 is shown in FIG. 8.

Figure 1:
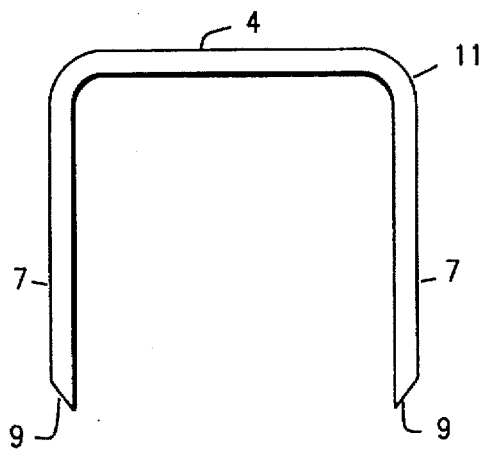
FIG. 1 depicts a U-shaped staple.
Figure 2:
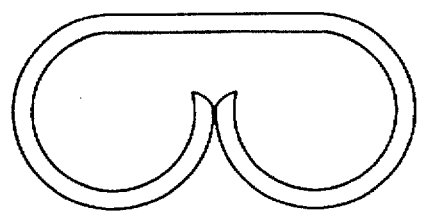
FIG. 2 shows the prior art staple of FIG. 1 after deformation to a B-shape.
Figure 3:
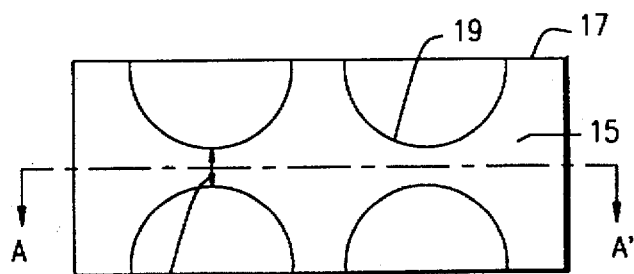
FIG. 3 is a top view of an anvil for deforming the staple of FIG. 1.
Figure 4:
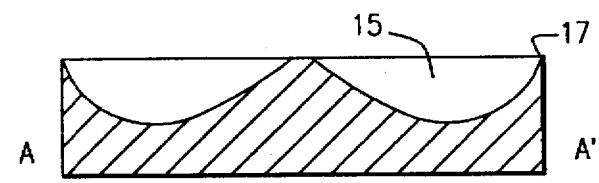
FIG. 4 is a side cross section view A–A' of the anvil groove of FIG. 3.

It should be noted that the width 88 of the narrow region 27 of the groove 19 of anvil 25 is significantly greater than the width 89 of the narrow region 19 of the conventional groove 15 of the anvil 17, as shown in FIG. 3. Specifically, since the width 89 of the narrow regions 19, as shown in FIG. 3, is sufficiently close to the diameter of leg 7 of staple 11 that during staple deformation the ends 9 cannot pass by each other and overlap, i.e., lie side by side, because the width 89 of the narrow regions 19 of groove 15 is not great enough to allow such passing while the legs 7 are confined in the groove 15.

Figure 5:
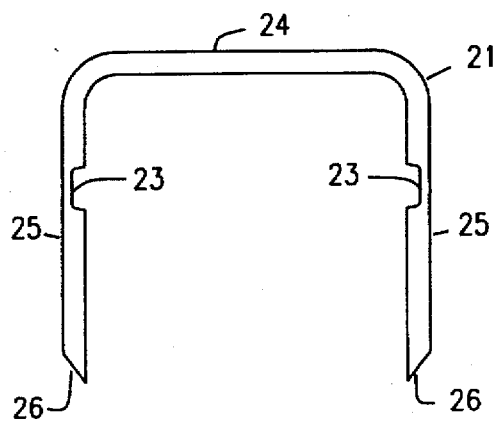
FIG. 5 depicts a Cook staple with leg lengths beyond the deformation zones which can lead to overlap for the deformed staple.

FIG. 5 shows a Cook staple 21 prior to deformation. Each leg 25 includes a deformation zone 23. Preferably, the lengths of the legs 25 between the tips 26 and the deformation zones 23 are sufficiently large as to achieve overlap of the tips 26 when the staple 21 is deformed.

Figure 6:
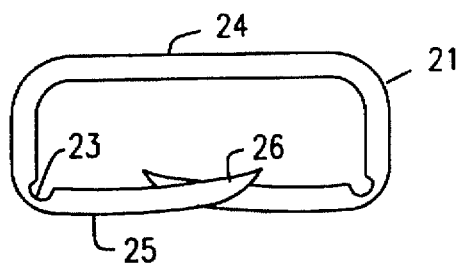
FIG. 6 depicts the staple of FIG. 5 after deformation showing the overlapping ends.

FIG. 6 shows a Cook staple 21 after it has been deformed. The deformation of the staple is typically accomplished by utilizing a staple pusher on a first side of the tissue to be stapled, and an anvil on an opposite side of the tissue to be stapled, a technique quite common in the art of stapling of internal tissues. It can be appreciated that overlap of the leg ends 26 helps to assure more uniform compression of tissues (not shown) enclosed by the staple 21. The overlap helps to assure that no tissue bulges from between the ends of the legs. Note that the tips 26 of the legs 25 deform so that they point towards the crown 24 of the staple 21.

It can be seen that there is no common plane that can contain the crown 24 of staple 21 and the legs 25 of the deformed staple 21 shown in FIG. 6. Since there is no such common plane, one or both of the staple legs must deform so that what is known in the prior art as twist develops. Twist of thin wire metal staples used in internal surgery is typically viewed as undesirable by those or ordinary skill in the art. For example, U.S. Pat. No. 4,607,638 to Crainich describes an improved technique to eliminate twist. (Col. 2, lines 36–39). On the other hand, twist is desirable in the present invention since it allows overlap of the ends 26 of the legs 25 of the deformed staple 21 shown in FIG. 6.

FIG. 7 is a top view of anvil 25. It can be seen that the width 88 of the narrow region 27 of groove 29 of anvil 25 is greater than the width 89 of the narrow region 19 of groove 15 in anvil 17. The width 88 of groove 29 is sufficiently great that the legs 25 of staple 21' can be confined by groove 29 while the tips 26 of the staple 21 lie side by side, i.e., overlap each other. Thus, during deformation of the staple 21 against anvil 25, the tips 26 can by-pass each other. A crossectional side view B–B' of groove 29 is shown in FIG. 8.

Figure 9:
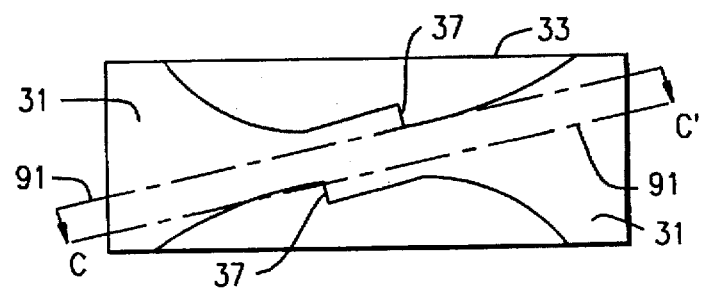
FIG. 9 shows a top view of the second type of anvil groove for use with the Cook staple.

FIG. 9 shows an alternative embodiment of the present invention wherein anvil 33 utilizes uniquely shaped grooves 31 in order to direct the ends 26 of the legs 25 of staple 21 so that they overlap during staple deformation. It can be seen from FIG. 9 that the tips 26 enter grooves 31 and are directed towards the ends 37 of the grooves 31. The legs 25 of staple 21 can be confined in grooves 31 when their tips 26 overlap. A side crossectional view C–C' of the anvil 33 of FIG. 9 is shown in FIG. 10, where it can be appreciated that a deformed staple with overlapping leg tips will result.

Figure 10:
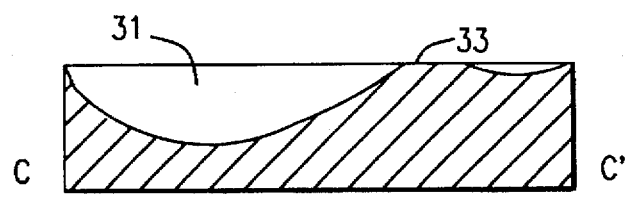
FIG. 10 shows a side cross section view C–C' of the anvil of FIG. 9.

The embodiment of FIGS. 9 and 10 achieves staple leg end overlap by ensuring that there is no common plane that includes the crown 90 of staple 21 and the center lines 91 of at least one of grooves 31 during staple deformation. This lack of a common plane leads to staple twist.

Figure 11:
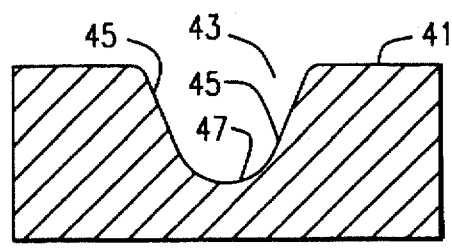
FIG. 11 shows a cross section view taken across the width of a groove in an anvil.

In FIG. 11, an anvil 41 is shown in a crossectional view taken across the width of groove 43. It can be seen in FIG. 11 that the sides of the grooves slope down from the top surface of the anvil to the bottom of the groove. This is typical of anvils formed by a stamping or coining operation. When we describe the legs of staples as being confined by grooves during deformation by interaction with anvils, the legs typically are located at or near the bottoms 47 of the grooves 42.

Figure 12:
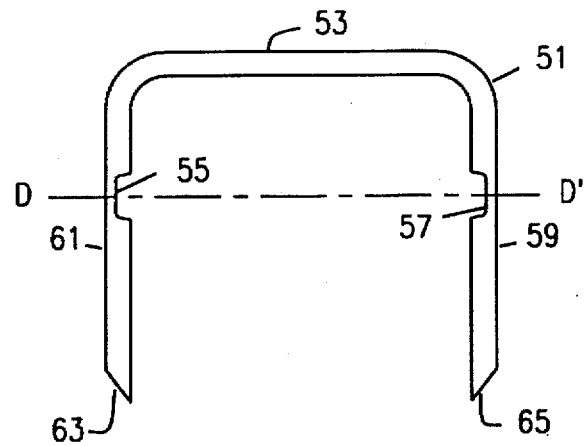
FIG. 12 shows a Cook staple in which the deformation zones have been rotated with respect to each other so that the legs will tend to bend into different planes.

In FIG. 12, a Cook staple 51 with crown 53 and legs 61 and 59 is shown. Section D–D' is shown taken across the deformation zones 55 and 57.

Figure 13:
FIG. 13 is a section through the legs of the staple shown in FIG. 12.

In FIG. 13, section D–D' of FIG. 12 is shown in cross section taken orthogonal to the plane of FIG. 12. It can be seen that the deformation zones 55 have been formed so that the tips 63 of the legs 59 and 61 shown in FIG. 12 tend to overlap when the staple 51 is deformed, so that there is no common plane including the crown 53 and both of the legs 59 and 61 of the staple 51 after deformation.

While the prior art is directed to assuring that twist—which is regarded in the prior art as undesirable misalignment of staple legs—and, specifically, leg end overlap is eliminated, it can be appreciated that the present invention takes an exactly opposite approach. Specifically, by ensuring that the staple leg ends overlap, it an be appreciated that a fully enclosed tissue region is achieved and maintained.

While the above describes the preferred embodiment of the present invention, it will be understood by those of ordinary skill in the art that numerous variations and additions are feasible. Such variations, additions and any modifications which fall within the spirit and the scope of the invention are intended to be covered by the following claims.

I claim:

1. A stapling arrangement for stapling tissue comprising:

at least one staple having a crown and two legs, each leg having a tip, each leg further including at least one deformation zone, each said at least one deformation zone being more susceptible to bending than regions of said leg adjacent to each said at least one deformation zone, an anvil having grooves for deforming said legs of said at least one staple, said anvil lying on the opposite side of said tissue from the side into which insertion of said tips of said legs of said at least one staple occurs, a staple pusher connected to said anvil and arranged to push on said crown of said at least one staple such that each of said tips of said legs of said at least one staple pass through said tissue and impinge against at least one groove of said anvil in order to deform said legs of said at least one staple, said grooves of said anvil being arranged to cause said deformation of said legs such that there is a single overlap of said legs of each staple with respect to each other formed by said deformation.

2. A stapling arrangement for stapling tissue comprising:

at least one staple having a crown and two legs, each said leg having a deformation zone and a tip and a region located between said deformation zone and said tip, an anvil with grooves for deforming said legs, a staple pusher movably connected to said anvil and including means for exerting a force upon said crown to push said tips of said legs through said tissue to force said tips against said grooves of said anvil;

said grooves deforming the legs of each of said at least one staple so as to bypass each other once such that said legs and said crown do not all lie in a common plane, said grooves also deforming said legs such that at least part of said regions of said each of said at least one staple are adjacent to each other.

* * * * *